US008425882B2

(12) United States Patent
Lou et al.

(10) Patent No.: US 8,425,882 B2
(45) Date of Patent: Apr. 23, 2013

(54) IN-SHOWER AND BATH COMPOSITIONS

(75) Inventors: Anjing Lou, Seymour, CT (US); Qiang Qiu, Trumbull, CT (US); Alexander Lips, New Canaan, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/060,437

(22) Filed: Apr. 1, 2008

(65) Prior Publication Data

US 2009/0247445 A1 Oct. 1, 2009

(51) Int. Cl.
*A61Q 19/10* (2006.01)

(52) U.S. Cl.
USPC ............................ 424/59; 424/401; 510/123

(58) Field of Classification Search ................ 510/123; 424/59, 401
See application file for complete search history.

(56) References Cited

U.S. PATENT DOCUMENTS

| | | | |
|---|---|---|---|
| 4,104,403 A | 8/1978 | Barker et al. | 424/365 |
| 4,385,049 A | 5/1983 | Cuca | 424/167 |
| 4,405,616 A | 9/1983 | Rajadhyaksha | 424/244 |
| 4,446,051 A * | 5/1984 | Berthod et al. | 516/23 |
| 4,606,913 A * | 8/1986 | Aronson et al. | 424/59 |
| 4,886,783 A | 12/1989 | Minaskanian et al. | 574/29 |
| 4,981,845 A | 1/1991 | Pereira | 514/557 |
| 5,118,845 A | 6/1992 | Peck et al. | 564/215 |
| 5,232,688 A | 8/1993 | Ziegler et al. | 424/59 |
| 5,387,417 A | 2/1995 | Rentsch | 424/401 |
| 5,412,004 A * | 5/1995 | Tachibana et al. | 524/27 |
| 5,612,044 A | 3/1997 | Suares et al. | 424/59 |
| 5,645,822 A | 7/1997 | Meyer et al. | 424/59 |
| 5,720,948 A | 2/1998 | Brucks et al. | 424/78.02 |
| 5,750,092 A | 5/1998 | Meyer et al. | 424/59 |
| 5,756,075 A | 5/1998 | Meyer | 424/59 |
| 5,833,973 A | 11/1998 | Dobkowski et al. | |
| 5,908,707 A | 6/1999 | Cabell et al. | |
| 5,977,194 A | 11/1999 | Mork et al. | 521/61 |
| 6,147,131 A | 11/2000 | Mork et al. | 521/61 |
| 6,231,837 B1 | 5/2001 | Stroud et al. | 424/59 |
| 6,303,834 B1 | 10/2001 | Mork et al. | 568/614 |
| 6,383,503 B1 | 5/2002 | Bleckmann et al. | 424/401 |
| 6,475,500 B2 | 11/2002 | Vatter et al. | 424/401 |
| 6,524,598 B2 | 2/2003 | Sunkel et al. | 424/401 |
| 6,548,050 B1 | 4/2003 | Bara | 424/64 |
| 6,685,952 B1 | 2/2004 | Ma et al. | 424/401 |
| 6,696,049 B2 | 2/2004 | Vatter et al. | |
| 6,699,488 B2 * | 3/2004 | Deckner et al. | 424/401 |
| 6,747,115 B2 | 6/2004 | Sakuta | 528/31 |
| 6,793,929 B2 | 9/2004 | Bleckmann et al. | 424/401 |
| 7,166,276 B2 * | 1/2007 | Stephens et al. | 424/63 |
| 7,175,835 B1 * | 2/2007 | Simoulidis et al. | 424/59 |
| 7,416,735 B2 * | 8/2008 | El-Nokaly et al. | 424/400 |
| 2002/0028184 A1 | 3/2002 | Sunkel et al. | 424/59 |
| 2002/0106385 A1 | 8/2002 | Vatter et al. | 424/401 |
| 2003/0170193 A1 | 9/2003 | Pate et al. | 424/70.12 |
| 2003/0211061 A1 | 11/2003 | Deckner et al. | |
| 2003/0211069 A1 | 11/2003 | Deckner et al. | 424/70.16 |
| 2003/0228339 A1 * | 12/2003 | El-Nokaly et al. | 424/401 |
| 2004/0146472 A1 | 7/2004 | Nakanishi | 424/70.12 |
| 2004/0228821 A1 | 11/2004 | Sunkel et al. | 424/70.12 |
| 2004/0235693 A1 | 11/2004 | Wei et al. | 510/130 |
| 2005/0008600 A1 | 1/2005 | Nakanishi et al. | 424/70.12 |
| 2005/0089486 A1 | 4/2005 | Spindler et al. | 424/59 |
| 2005/0118218 A1 | 6/2005 | Cassin | 424/401 |
| 2006/0013790 A1 | 1/2006 | Shimizu | 424/70.12 |
| 2006/0057927 A1 | 3/2006 | Kang et al. | 445/46 |
| 2006/0078524 A1 | 4/2006 | Midha et al. | 424/70.12 |
| 2006/0078527 A1 * | 4/2006 | Midha et al. | 424/70.27 |
| 2006/0079422 A1 | 4/2006 | Midha et al. | 510/130 |
| 2006/0100004 A1 | 5/2006 | Kim et al. | 455/575.3 |
| 2006/0111490 A1 | 5/2006 | Fonolia Moreno | 524/211 |
| 2006/0120979 A1 | 6/2006 | Rubin | 424/62 |
| 2006/0127344 A1 | 6/2006 | Zofchak et al. | 424/70.31 |
| 2006/0159649 A1 * | 7/2006 | Sabin et al. | 424/70.16 |
| 2007/0009463 A1 | 1/2007 | Niebauer et al. | 424/70.7 |
| 2007/0020217 A1 | 1/2007 | Themens | 424/70.12 |
| 2007/0173599 A1 | 7/2007 | Liu et al. | 524/588 |
| 2008/0145436 A1 * | 6/2008 | Lorant | 424/489 |
| 2008/0299058 A1 | 12/2008 | Saito et al. | 424/59 |
| 2008/0299156 A1 | 12/2008 | Fares et al. | 424/401 |
| 2008/0311058 A1 | 12/2008 | Lou et al. | 424/59 |
| 2009/0155321 A1 | 6/2009 | Harichian et al. | 424/401 |
| 2009/0226498 A1 | 9/2009 | Flugge-Berendes et al. | 424/411 |
| 2009/0247445 A1 | 10/2009 | Lou et al. | 510/159 |

FOREIGN PATENT DOCUMENTS

| | | |
|---|---|---|
| DE | 100 49 041 | 4/2002 |
| EP | 0 009404 | 4/1980 |
| EP | 0 160 430 | 11/1985 |

(Continued)

OTHER PUBLICATIONS

1- Shin-Etsu Silicones for Personal Care. Product Brochure, KSG Series, 2004. 2- Shin-Etsu Silicones for Personal Care. Product Brochure, Emulsefiers Series, 2004.*
Lotioncrafter; Cyclomethicone and Essential Oils.*
Co-pending application for: Applicant: Lou et al.; U.S. Appl. No. 11/820,382, filed Jun. 18, 2007.
International Search Report and Written Opinion on Application No. PCT/EP2009/053578 dated Jul. 29, 2009.
Co-pending Application: Applicant: Lou et al.; U.S. Appl. No. 12/784,046, filed May 21, 2010.
Co-pending Application: Applicant: Lou et al.; U.S. Appl. No. 12/814,855, filed Jun. 14, 2010.
Co-pending Application: Applicant: Lou et al.; U.S. Appl. No. 11/820,382, filed Jun. 18, 2007.
Co-pending Application: Applicant: Lou et al.; U.S. Appl. No. 12/402,238, filed Mar. 11, 2009.
Co-pending Application: Applicant: Carnali; U.S. Appl. No. 12/627,566, filed Nov. 30, 2009.
Co-pending Application: Applicant: Lou et al., U.S. Appl. No. 12/855,348, filed Aug. 12, 2010.
Co-pending Application: Applicant: Carnali et al., U.S. Appl. No. 12/909,874, filed Oct. 22, 2010.
*Shin-etsu Silicones for Personal Care*: Shin-Etsu Product Brochure, Emulsifiers Series; pp. 1-5.
Abstract of DE 100 49 041—published Apr. 11, 2002.
Abstract of JP 57-091733—published Jun. 8, 1982.
Abstract of WO 03/022235—published Mar. 20, 2003.

*Primary Examiner* — Mark Eashoo
*Assistant Examiner* — M. Reza Asdjodi
(74) *Attorney, Agent, or Firm* — Edward A. Squillante, Jr.

(57) ABSTRACT

In-the-shower or in-the-bath compositions having a high internal phase emulsion are described. The high internal phase emulsion is a water-in-oil emulsion where active is present in the water phase. The compositions have an initial viscosity which is low and they are suitable to thicken when being applied in the presence of water.

22 Claims, No Drawings

FOREIGN PATENT DOCUMENTS

| | | |
|---|---|---|
| EP | 0 818 190 | 1/1998 |
| EP | 1 741 422 A | 1/2007 |
| GB | 1 465 528 | 2/1974 |
| GB | 1 465 529 | 2/1974 |
| GB | 1 465 530 | 2/1974 |
| GB | 2 139 919 | 11/1984 |
| GB | 2 181 737 A | 4/1987 |
| JP | 57-091733 | 6/1982 |
| JP | 11-158032 | 6/1999 |
| JP | 2005-314327 | 11/2005 |
| WO | 96/21721 A | 7/1996 |
| WO | 97/33560 | 9/1997 |
| WO | 01/00141 A | 1/2001 |
| WO | 01/89464 | 11/2001 |
| WO | 03/022235 | 3/2003 |
| WO | 03/075879 | 9/2003 |
| WO | 2008/155228 A | 12/2008 |
| WO | 2009/121787 | 10/2009 |
| WO | 2010/009989 | 1/2010 |
| WO | 2010/045163 | 4/2010 |

\* cited by examiner

IN-SHOWER AND BATH COMPOSITIONS

FIELD OF THE INVENTION

The present invention is directed to a composition suitable for use in the shower and bath. More particularly, the present invention is directed to a composition comprising a water-in-oil and high internal phase emulsion that may be formulated with an active or skin benefit agent within the water phase. The composition can be used to deliver the active while showering or bathing, and unexpectedly, the composition thickens during application and in the presence of water to ensure that active is not readily rinsed from the skin after application.

BACKGROUND OF THE INVENTION

Skin conditioning compositions that provide, for example, moisturizing benefits are known. Typically, such conditioning compositions are in the form of lotions meant to be applied to the skin subsequent to bathing and throughout the day if necessary.

Certain consumers find it desirable to deliver skin conditioning benefits via an in-the-shower or in-the-bath lotion. Unfortunately, however, such lotions are often readily rinsed from the skin leaving little, if any, benefit agent on the skin after showering or bathing. Attempts to prevent the washing off of such agents in the shower involve formulating compositions with high initial viscosities (i.e., $\geq 10,000$ cps). Unfortunately, such compositions are not easy to apply due to the thickness of the composition prior to application.

It is of increasing interest to develop a composition suitable to deliver an active or skin benefit agent while showering or bathing, and particularly, where the composition is easy to spread and apply. This invention, therefore, is directed to a composition comprising a water-in-oil and high internal phase emulsion that can be used to deliver an active while showering or bathing. The composition has a low initial viscosity (i.e., <6500 cps), and unexpectedly, the composition thickens during application and in the presence of water to ensure that active is not readily rinsed from the skin after application. Also, the composition of this invention surprisingly yields a pleasant and silky feeling upon application.

ADDITIONAL INFORMATION

Efforts have been disclosed for making insoluble skin conditioning compositions. In U.S. Pat. No. 6,699,488, rinseable compositions with high internal phase emulsions are described.

Other efforts have been disclosed for making skin care compositions. In U.S. Pat. No. 6,696,049, cosmetic compositions with emulsifying cross-linked siloxane elastomer are described.

Still other efforts have been disclosed for making skin care compositions. In U.S. Pat. No. 5,908,707, cleaning articles having a high internal phase inverse emulsion are described.

Even other efforts have been disclosed for making skin care compositions. In U.S. Pat. No. 5,833,973, skin treatment compositions with a cross-linked non-emulsifying siloxane elastomer are described.

None of the additional information above describes a composition with a high internal phase emulsion (HIPE) having an active or skin benefit agent within the water phase whereby the composition thickens during application and in the presence of water to ensure that active is not readily rinsed off from the skin after the composition is applied while showering or bathing.

SUMMARY OF THE INVENTION

In a first aspect, the present invention is directed to a HIPE composition comprising:
  (a) water;
  (b) emulsifier;
  (c) steric stabilizer;
  (d) depletion stabilizer; and
  (e) oil
wherein the composition thickens when being applied in the presence of water.

In a second aspect, the present invention is directed to an in-the-shower or in-the-bath composition comprising the HIPE of the first aspect of this invention.

In a third aspect, the present invention is directed to a method for topically delivering an active or skin benefit agent with the in-the-shower or in-the-bath composition of the second aspect of this invention.

All other aspects of the present invention will more readily become apparent upon considering the detailed description and examples which follow.

HIPE, as used herein, means a high internal phase, water-in-oil emulsion where the emulsion is at least about 73% by weight water when deplete of active. In-the-shower and in-the-bath compositions, as used herein, are meant to mean end use compositions comprising the HIPE with an active or skin benefit agent in the water phase of the HIPE, whereby the same are suitable for use with humans to enhance a skin characteristic. Such compositions are meant to include compositions that may be applied, and preferably, are applied while showering or bathing, but optionally, not within the direct flow of water. The HIPE of this invention (when comprising active) typically makes up at least about 80% by weight of the total weight of the in-the-shower or in-the-bath composition (i.e., collectively, end use compositions).

Skin, as used herein, is meant to include skin on the face, neck, chest, back, arms, hands, legs and scalp (including hair). Steric stabilizer, as used herein, means an ingredient like a polymer (including elastomer) that prevents coalescence of water thereby stabilizing the HIPE. Active and skin benefit agent are meant to mean the same, and thus, may be used interchangeably, where the same include an ingredient that improves a skin characteristic, including a tanning agent like dihydroxyacetone. Depletion stabilizer is meant to mean an agent that reduces the hydrophobicity of oil and that prevents water droplet accumulation. Non-emulsifying elastomer is defined to mean a siloxane from which polyoxyalkylene units are absent (like DC9045 made available from Dow Chemical). Capillary number means the ratio of viscous force to surface tension force between two immiscible and flowable phases.

Unless explicitly stated otherwise, all ranges described herein are meant to include all ranges subsumed therein. The term comprises is meant to encompass the terms consisting essentially of and consisting of. Furthermore, unless defined otherwise, the amount of polymer or elastomer used means the amount of cross-linked polymer and carrier oil added as a mixture whereby the cross-linked polymer typically makes up from about 10 to about 35% by weight of the mixture, including all ranges subsumed therein. Unless explicitly stated otherwise, viscosity, as used herein, means a fluid's internal resistance to flow taken at a shear rate of $1\ S^{-1}$ at ambient temperature with a strain controlled parallel plate rheometer (like those sold by T.A. Instruments under the Ares name). Results described herein are based on applying about 3 mg of composition to about every 1 $cm^2$ of skin.

DETAILED DESCRIPTION OF THE PREFERRED EMBODIMENT

There is no limitation with respect to the type of emulsifier that may be used in this invention other than that the emulsifier is suitable for use in a HIPE which may be used in an end use composition suitable for topical application. Such emulsifier often has an HLB of less than about 9, preferably less than about 7, and most preferably, less than about 5. Illustrative examples of the type of emulsifier that may be used in this invention include those generally classified as polyether modified silicone surfactants like PEG/PPG-20/22 butyl ether dimethicone, PEG-3 dimethicone, PEG-9 methyl ether dimethicone, PEG-10 dimethicone, mixtures thereof or the like. The emulsifiers are made available from suppliers like Shin-Etsu and sold under the names KF-6012, KF-6015, KF-6016, and KF-6017, respectively. In an often preferred embodiment, the emulsifier used in this invention is PEG-10 dimethicone or KF-6017.

Typically, the emulsifier makes up from about 0.05 to about 12%, and preferably, from about 0.1 to about 10%, and most preferably, from about 0.5 to about 4% by weight of the HIPE, based on total weight of HIPE and including all ranges subsumed therein.

The steric stabilizer that may be used in this invention to prevent coalescence of water and to stabilize the HIPE of this invention is preferably an elastomer. Such a steric stabilizer is one which preferably has a refractive index of greater than about 1.4 at 25° C. Moreover, the steric stabilizer is often a cross-linked elastomer (such as a polyether and/or polyglycerine cross-linked elastomer) where the cross-linking group preferably has a chain length from about 8 to about 26 carbon atoms.

Often preferred steric stabilizers suitable for use in this invention are Dimethicone/PEG-10/15 Crosspolymer in Dimethicone (KSG-210 or KSG-240), Dimethicone Polyglycerin-3 Crosspolymer in Dimethicone (KSG-710), mixtures thereof or the like. Such steric stabilizers are made commercially available, and especially, from suppliers like Shin-Etsu.

Typically, the amount of steric stabilizer (ie., including carrier) employed is from about 0.1 to about 25%, and preferably, from about 0.2 to about 15%, and most preferably, from about 0.5 to 8%, based on total weight of the HIPE and including all ranges subsumed therein. In a preferred embodiment, the steric stabilizer used in the HIPE of this invention is KSG-210 or a derivative or mimic thereof.

The HIPE of the present invention further comprises a depletion stabilizer which often is an alkyl modified cross-linked elastomer (such as a polyether and/or polyglycerine cross-linked elastomer) where the cross-linking group preferably has a chain length from about 8 to about 26 carbon atoms.

Illustrative examples of the types of depletion stabilizer suitable for use in this invention include PEG-15/Lauryl Dimethicone Crosspolymer in Mineral Oil (KSG-310), PEG-15/Lauryl Dimethicone Crosspolymer and Isododecane (KSG-320), PEG-15/Lauryl Dimethicone Crosspolymer in Triethylhexanoin (KSG-330), PEG-10/Lauryl Dimethicone Crosspolymer and PEG 15/Lauryl Dimethicone Crosspolymer in Squalane (KSG-340), Lauryl/Dimethicone/Polyglycerine-3 Crosspolymer in Triethylhexanoin (KSG-830), Lauryl Dimethicone/Polyglycerine-3 Crosspolymer in Squalene (KSG-840), mixtures thereof or the like.

When used, the amount of depletion stabilizer (including carrier) employed is typically from about 0.25 to about 20%, and preferably, from about 0.1 to about 15%, and most preferably, from about 0.5 to about 10% by weight, based on total weight of HIPE and including all ranges subsumed therein.

Oil suitable for use in the HIPE of this invention is limited only to the extent that the same can be used in a HIPE that will be topically applied. The oil used in the HIPE of this invention is preferably silicon-based, and particularly, one classified as a D4, D5, or D6 cyclodimethicone or a mixture thereof. Other preferred oils suitable for use in this invention include dimethicone-based oils having a viscosity from about 3 cps to about 100 cps at ambient temperature and as determined on a Ubbelohde Viscometer. Such oils may be used alone or in combination with other oils suitable for use in topical compositions, like mineral oil and/or paraffin oil.

The oil within the HIPE of this invention typically makes up from about 0.5 to about 23%, and preferably, from about 5 to about 18%, and most preferably, from about 10 to about 15% by weight of the HIPE, based on total weight of the HIPE and including all ranges subsumed therein.

In an especially preferred embodiment, less than about 60%, and preferably, less than about 50%, and most preferably, from about 2 to about 35% by weight of the total oil in the HIPE of this invention is provided as carrier with elastomer.

When an end use composition comprising the HIPE of the present invention is desired, the HIPE typically further comprises actives or skin benefit agents suitable for addition to the water phase (i.e., water soluble actives). Such actives include self-tanning compounds like dihydroxyacetone (DHA), vitamins (especially, niacinamide), moisturizers like sugar derivatives, natural extracts, mixtures thereof or the like.

Illustrative sugar derivatives that may be used include alkylated versions of glucose, sucrose, galactose, xylose, ribose, fructose or mannose, or the like or a mixture thereof. The often preferred sugar derivative is methylglucose. The natural extracts that may be used include, for example, extract of pea, cucumber, comfrey, chamomile, or a mixture thereof.

Other actives suitable for use in the water phase of the HIPE of this invention include alpha- and/or beta-hydroxycarboxylic acids, as well as antioxidants. When hydroxycarboxylic acids are employed, they preferably include α-hydroxyethanoic acid, α-hydroxypropanoic acid, α-hydroxyhexanoic acid, α-hydroxyoctanoic acid, α-hydroxydecanoic acid, α-hydroxydodecanoic acid, α-hydroxytetradecanoic acid, α-hydroxyhexadecanoic acid, γ-hydroxyoctadecanoic acid, α-hydroxyeicosanoic acid, α-hydroxydocosanoic acid, α-hydroxyhexacosanoic acid, α-hydroxyoctacosanoic acid, acids thereof, salts thereof, mixtures thereof or the like. Antioxidants suitable for use include diadzein, genistein, gallic acid, epicatechin, epigallacatechin, epicatechin-3-gallate, epigallocatechin-3-gallate, mixtures thereof or the like.

Typically, the amount of active or skin benefit agent used in the water phase of the HIPE of this invention is from about 0.5 to less than about 24%, and preferably, from about 2 to about 18%, and most preferably, from about 7 to about 13%, based on total weight of the HIPE and including all ranges subsumed therein. An often preferred active used in this invention is DHA.

Water will typically make up the balance of the HIPE, and should make up at least about 73% (when no active is present) to typically no more than about 96% by weight of the HIPE, including all ranges subsumed therein.

Optional but additional additives may be combined with the HIPE of the present invention (as actives or co-actives within the water phase or oil phase, or as additives in order to yield a desired end use composition). For example, end use compositions prepared with the HIPE of this invention may optionally contain a skin conditioning agent. These agents may be selected from humectants or emollients.

Suitable humectants are polyhydric alcohols intended for moisturizing, reducing scaling and stimulating removal of built-up scale from the skin. Typical polyhydric alcohols include polyalkylene glycols and more preferably glycerol (or glycerin), alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin. Amounts of humectant may range (if used) anywhere from about 0.01 to 12%, preferably from about 0.01 to about 10%, optimally from about 0.75 to about 5% by weight of the end use composition. In yet another preferred embodiment, glycerin is the active employed, either alone or in a mixture with DHA.

When the conditioning agent is an emollient it may be selected from hydrocarbons, fatty acids, fatty alcohols and esters. Petrolatum is the most preferred hydrocarbon type of emollient conditioning agent. Other hydrocarbons that may be employed include mineral oil, polyolefins such as polydecene, and paraffins such as isohexadecane (e.g., Permethyl 99® and Permethyl 101®).

Fatty acids and alcohols suitable for use often have from 10 to 30 carbon atoms. Illustrative of this category are pelargonic, lauric, myristic, palmitic, steric, isosteric, hydroxysteric, oleic, linoleic, ricinoleic, arachidic, behenic and erucic acids and alcohols.

Oily ester emollients suitable for use in end use compositions made with the HIPE of this invention can be those selected from one or more of the following classes:
1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalene, Kikui oil and soybean oil.
2. Acetoglyceride esters, such as acetylated monoglycerides.
3. Ethoxylated glycerides, such as ethoxylated glyceryl monostearate.
4. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
5. Alkenyl esters of fatty acids having 10 to 20 carbon atoms. Examples thereof include oleyl myristate, oleyl stearate, and oleyl oleate.
6. Ether-esters such as fatty acid esters of ethoxylated fatty alcohols.
7. Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.
8. Wax esters such as beeswax, spermaceti, myristyl myristate, stearyl stearate.

Still other illustrative actives suitable for use with the HIPE of this invention (in the water phase, oil phase or both) include resorcinols, retinoids, including retinoic acid, retinal and retinyl esters as well as conjugated linoleic acid (CLA) and/or petroselinic acid, including derivatives thereof.

CLA isomers of the greatest interest in the present invention are cis 9, trans 11-linoleic acid and trans 10, c is 12-linoleic acid Hereinafter the term "9,11-linoleic" or "10,12-linoleic" shall mean preferentially these two main isomers, but will include lesser amounts of the remaining isomers, particularly when obtained or derived from a natural source.

In accordance with the present invention, 9,11-linoleic acid and 10,12-linoleic acid may be formulated into the HIPE of this invention either as the free acid, as individual chemical derivatives, or as combinations of the free acid and derivative.

By "c9, t11, and 10, c12 isomer enriched CLA" is meant that at least 30% by weight of the total CLA (and/or CLA moieties) that may be present in the HIPE is in the form of the cis 9, trans 11 and trans 10, c is 12 isomers. Preferably, and when used, at least 40%, most preferably at least 50%, by weight of the total CLA and/or CLA moieties present in the HIPE, is in the form of the aforementioned isomers.

Commercially, CLA is available as Clarinol® A-80 and A-95 from Loders-Croklaan, Channahon, Ill. and Neobee® CLA 80 and 90 from, North Field, Ill.

Preservatives can desirably be incorporated into the in-the-shower or in-the-bath compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the end use compositions described herein. Suitable traditional preservatives are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, propyl paraben, imidazolidinyl urea, sodium dehydroxyacetate and benzyl alcohol. The preservatives should be selected having regard for the use of the HIPE and possible incompatibilities between the preservatives and other ingredients in the emulsion. Preservatives are preferably employed in amounts ranging from 0.01% to 2% by weight of the end use composition.

Sunscreens may be used (in any desirable combination) in the end use compositions and they include those materials commonly employed to block ultraviolet light. Illustrative compounds are PABA, cinnamate and salicylate. For example, avobenzophenone (Parsol 1789®) octyl methoxycinnamate and 2-hydroxy-4-methoxyl benzophenone (also known as oxybenzone) can be used. Octyl methoxycinnamate, 2-ethylhexyl-p-methoxycinnamate, and 2-hydroxy-4-methoxy benzophenone are all commercially available. Others which may be used include octocrylene, butyl-methoxydibenzoyl methane and phenylbezimidazole sulfonic acid. The exact amount of sunscreen employed in the compositions can vary depending upon the degree of protection desired from the sun's UV radiation.

Even other optional additives that may be used with the end use compositions of this invention and they include physical scatterers (like $TiO_2$ and/or ZnO), chelators (like EDTA), microspheres (e.g., polyethylene based spheroids sold under the name CL-2080; ethylene and methacrylate based spheroids sold under the names SPCAT-12 and DSPCS-12, respectively, made available by Kobo Industries), anti-inflammatory agents (including the standard steroidal and non-steroidal types), and dispersants (e.g., PEG-100 stearate and/or NaCl).

Typically, the optional additives used to make the end use composition of this invention, collectively, make up less than about 15%, and preferably, less than about 12%, and most preferably, less than about 10% by weight of the skin care composition, based on total weight of the end use composition and including all ranges subsumed therein. In a preferred embodiment the HIPE of this invention makes up at least about 85% by weight of the end use composition, and most preferably, at least about 88 to about 96% by weight of the end use composition, including all ranges subsumed therein.

Minor adjunct ingredients may also be included such as fragrances, antifoam agents, and colorants, each in their effective amounts to accomplish their respective functions. In a preferred embodiment, the end use compositions of the present invention are substantially free (i.e., less than about 1.0% by weight) of non-emulsifying elastomer, and most preferably, free of non-emulsifying elastomer.

When making the compositions of the present invention, the desired ingredients can be mixed in no particular order and usually at temperatures from about ambient to about 65° C. and under atmospheric pressure. In a preferred embodiment, however, water is added to oil.

The in-the-shower and in-the-bath compositions prepared with the HIPE of this invention preferably have an initial viscosity of less than about 6000 cps, and most preferably, from about 10 to about 4000 cps, including all ranges subsumed therein.

The in-the-shower and in-the-bath compositions of the present invention typically have an initial (i.e., before application) water droplet diameter size from about 40 to about 150 microns whereby after routine application in the presence of water, the same will unexpectedly have a water droplet diameter size reduction such that the final water droplet diameter size (i.e., the diameter of water droplets in the HIPE forming a portion of the end use compositions and during application) is unexpectedly from about 5 to about 20, and preferably, from about 10 to about 15 times smaller than the initial water droplet diameter size. In an especially preferred embodiment, the final water droplet diameter size in the end use compositions during application is greater than about 2.5 and less than about 15 microns. Furthermore, during application and while showering or bathing, the end use compositions of the present invention absorb water (in the water phase of the HIPE) and from about 1 to about 80% but often from about 10 to about 80% by weight of water present in the compositions during application is absorbed, based on total weight of water in the compositions during application and including all ranges subsumed therein. In a preferred embodiment, from about 5% to about 65%, and most preferably, from about 20% to about 40% by weight of the total amount of water in the composition during application is absorbed whereby the absorbed water also has a droplet diameter size (when the end use composition is being applied) from about 2.5 to about 15 microns.

In a most especially preferred embodiment, the end use compositions of the present invention have a Capillary Number greater than 1 and less than about 1.6. Such compositions have a contact angle of less than about 1000, preferably, less than about 90°, and most preferably, from about 65° to about 90° against water as determined using a Kruss OCA-20 Ganiometer. The end use compositions unexpectedly have a viscosity greater than about 6,500 cps to about 125,000 cps, and preferably, from about 8,000 cps to about 120,000 cps, and most preferably, from about 25,000 cps to about 60,000 cps during application and including all ranges subsumed therein. The end use compositions of this invention yield a pleasant and silky feeling upon application and are surprisingly easy to spread on wet skin and result in less active being washed off when applying during the showering or bathing process. In fact, HPLC analysis of the compositions of the present invention that deposited on skin after being applied during conventional bathing or showering revealed that at least about 18%, and preferably, at least about 25%, and most preferably, at least about 30% of active in the composition prior to applying remained on the skin.

The packaging for the compositions of this invention is not limited and often is a bottle, tube, roll-ball applicator, squeeze container or lidded jar.

The examples below are provided to illustrate the invention and are not intended to limit the scope of the claims.

Example 1

A control in-the-shower composition was prepared by mixing the following ingredients with moderate shear at ambient temperature.

| Ingredients | % by Weight |
| --- | --- |
| Glycerin | 8 |
| Emulsifier | 2.5 |
| Polyether/polyglycerine cross-linked elastomer | 2 |
| Non-emulsifying elastomer | 5 |
| Silicone oil (D5) | 6 |
| Dimethicone oil | 1 |
| Steric stabilizer | 1 |
| Spheroid | 1-3 |
| Water | balance |

Panelists concluded that the control end use composition comprising a high internal phase emulsion having a non-emulsifying elastomer and no depletion stabilizer was very difficult to spread on wet skin and the same displayed a contact angle of greater than 130° against water.

Example 2

In-the-shower compositions consistent with the present invention were made by mixing the following ingredients via a process that was similar to the process described in Example 1.

| Ingredient | % by Weight |
| --- | --- |
| Glycerin | 8 |
| Emulsifier | 1.5 |
| Depletion stabilizer | 1 |
| Steric stabilizer | 1.5 |
| Silicone oil (D5) | 6-8 |
| Dimethicone oil | 1 |
| Spheroid | 1-3 |
| Dihydroxyacetone | 10 |
| Water | balance |

The compositions prepared in this example were applied on skin in the presence of water. Analysis (HPLC) of composition deposited on skin unexpectedly revealed that at least about 30-40% active remained on skin after washing. Control compositions, when used under substantially the same conditions, were difficult to spread, failed to deposit and washed off. The compositions of this example were easy to apply and spread very well, yielding a pleasant and silky feeling after application and even in the presence of water. Twenty (20) grams of the compositions prepared unexpectedly absorbed an average of about 0.5 grams of water per minute. The compositions had contact angles of circa 800 and water droplet sizes at about 8 microns during application.

What is claimed is:

1. A high internal phase water-in-oil emulsion, HIPE, consisting essentially of:
   (a) water;
   (b) emulsifier having an HLB of less than 9;
   (c) from about 0.1 to about 25% by weight steric stabilizer, the steric stabilizer being polyethylene glycol or polyglycerine cross-linked elastomer having a chain length from about 8 to about 26 carbon atoms;
   (d) from about 0.25 to about 20% by weight depletion stabilizer, the depletion stabilizer being an alkyl modified cross-linked elastomer having a polyethylene glycol or polyglycerine crosslinking group with a chain length from about 8 to about 26 carbon atoms; and
   (e) oil comprising $D_4$, $D_5$, $D_6$ cyclodimethicone or a mixture thereof
   wherein the HIPE thickens when being topically applied in the presence of water and is capable to carry and deliver an active while showering or bathing and further wherein the emulsion is substantially free of non-emulsifying elastomer and comprises a water droplet size that is from about 10 to about 15 times smaller than about 40 to about 50 microns during topical application.

2. The emulsion according to claim 1 wherein the emulsion further comprises in its water phase an active suitable to enhance a skin characteristic.

3. The emulsion according to claim 2 wherein the active is dihydroxyacetone, glycerin, vitamin, a sugar derivative, natural extract, or a mixture thereof.

4. The high internal phase water-in-oil emulsion according to claim 1 wherein the water phase is suitable to absorb water.

5. An in-the-shower or in-the-bath composition comprising:
 (a) a high internal phase water-in-oil emulsion consisting essentially of:
  (i) water;
  (ii) emulsifier having an HLB of less than 9;
  (iii) from about 0.1 to about 25% by weight steric stabilizer, the steric stabilizer being polyethylene glycol or polyglycerine cross-linked elastomer having a chain length from about 8 to about 26 carbon atoms;
  (iv) from about 0.25 to about 20% by weight depletion stabilizer, the depletion stabilizer being an alkyl modified cross-linked elastomer having a polyethylene glycol or polyglycerine crosslinking group with a chain length from about 8 to about 26 carbon atoms; and
  (v) oil comprising $D_4$, $D_5$ or $D_6$ cyclodimethicone or a mixture thereof, and
 (b) active
wherein the composition thickens when being topically applied in the presence of water and the high internal phase water-in-oil emulsion, HIPE, is capable to carry and deliver active while showering or bathing and further wherein the composition is substantially free of non-emulsifying elastomer and the emulsion comprises a water droplet size that is from about 10 to about 15 times smaller than about 40 to about 50 microns during topical application.

6. The composition according to claim 5 wherein the active is present in the water of the emulsion.

7. The composition according to claim 5 wherein the composition comprises resorcinol, retinoid, conjugated linoleic acid, petroselinic acid or a mixture thereof in the water, oil or both.

8. The composition according to claim 5 wherein the composition comprises dihydroxyacetone, vitamin, sugar derivative, hydroxcarboxylic acid, natural extract or a mixture thereof in the water of the emulsion.

9. The composition according to claim 5 wherein the emulsion makes up at least about 85% by weight of the composition.

10. The composition according to claim 5 wherein the emulsion makes up form about 88 to about 96% by weight of the composition.

11. The composition according to claim 5 wherein the water of the emulsion comprises humectant.

12. The composition according to claim 11 wherein the humectant is glycerin.

13. The composition according to claim 5 wherein the composition has an initial viscosity of less than about 6,000 cps and a viscosity greater than about 6,500 to about 125,000 cps during application.

14. The composition according to claim 5 wherein water is absorbed by the water phase in the water-in-oil HIPE of the composition during application while showering or bathing.

15. The composition according to claim 14 whereby the absorbed water has a droplet diameter size when the composition is being applied from about 2.5 to about 15 microns.

16. The composition according to claim 5 wherein the composition has water droplets that are from about 40 to about 150 microns before application and from about 5 to about 20 microns during application.

17. The composition according to claim 5 wherein the composition has a capillary number from about 1 to about 1.6.

18. The composition according to claim 5 wherein the composition has a contact angle of less than about 100° against water.

19. A method for delivering active to a consumer comprising the step of applying the composition of claim 5 to skin of the consumer while bathing or showering.

20. The method according to claim 19 wherein the active is DHA, niacinamde, moisturizing agent or mixtures thereof.

21. The composition according to claim 5 wherein the active is DHA, niacinamide, moisturizing agent or mixtures thereof.

22. The composition according to claim 5 wherein the emulsion is at least about 73% water when deplete of active and the emulsion with active makes up at least about 80% by weight of the total weight of the in-the-shower or the in-the-bath composition and further wherein the emulsion comprises a water droplet size that is from about 10 to about 15 times smaller than about 40 to about 50 microns during topical application.

* * * * *